United States Patent

Cloutier

[11] 4,211,228
[45] Jul. 8, 1980

[54] MULTIPURPOSE TIBIAL TEMPLATE

[76] Inventor: Jean-Marie Cloutier, 12 Aberdeen, Montreal, Quebec, Canada, H3Y 3A4

[21] Appl. No.: 6,073

[22] Filed: Jan. 24, 1979

[51] Int. Cl.² .......................... A61B 17/00; A61F 1/24
[52] U.S. Cl. ................................. 128/303 R; 3/1.911; 128/92 E; D24/26
[58] Field of Search ............... 128/303 R, 92 E, 92 C; 3/1.911, 1.91, 1.9; D24/26

[56] References Cited

PUBLICATIONS

Orthopedic Catalog, Richards Mfg. Co., Inc., 1974, The Richards Modular Knee system, pp. 60-67.
Zimmer Product Encyclopedia, Warsaw, Ind., Jun. 1978, "Geo-Patella/Geo-Tibial Total Knee", Geometric Total Knee and Multi-Radius Total Knee, (pp. A8-9–A106).

*Primary Examiner*—Ronald L. Frinks

[57] ABSTRACT

A multipurpose template comprising: a Y-shaped element comprising a flat handle integrally extended at one end by two flat, elongated prongs, which elongated prongs are symmetrically arranged with respect to a vertical plane passing through the axis of the Y-shaped element perpendicularly to the general plane thereof; an alignment rod fixable onto the flat handle near its integrally extended end, which alignment rod is substantially perpendicular to the general plane of the Y-shaped element; and a set of provisional plateaus of different thicknesses for each prong, for determining the thickness of condylar bearing members to be used in the total knee prosthesis. This template is particularly useful in total knee arthroplasty for determining the desired location of the tibial prosthesis component on the patient's tibia, the width or the amount of tibial eminence to be preserved, the planes of tibial plateau osteotomies, the location of the fixation studs of the tibial prosthesis component and the appropriate thickness of the tibial prosthesis component to be used, as well as for testing the range of motion of the knee prior to installing the tibial component and testing the latter as such prior to fixing it on the patient's tibia.

4 Claims, 5 Drawing Figures

MULTIPURPOSE TIBIAL TEMPLATE

The present invention relates to a multipurpose tibial template useful in total knee arthroplasty for determining the desired location of the tibial prosthesis component on the patient's tibia, the width or the amount of tibial eminence to be preserved, the planes of tibial plateau osteotomies, the location of the fixation studs of the tibial prosthesis component and the appropriate thickness of the tibial prosthesis component to be used, as well as for testing the range of motion of the knee prior to installing the tibial component and testing the latter as such prior to fixing it on the patient's tibia.

The invention more particularly relates to a multipurpose tibial template especially designed for use in the implantation of an adjustable total knee prosthesis including two removable condylar bearing members, such as disclosed in copending patent application Ser. No. 4,556 filed on Jan. 18, 1979 in the name of the same inventor.

Tibial alignment guides for indicating and checking the proper plane of horizontal resection for the tibial plateaus as well as tibial spacer guides for determining the appropriate thickness of bone to be resected to allow for correct implantation of the femoral and tibial components of a total knee prosthesis, are known and commonly used in total knee arthroplasty. Various models of such tibial alignment and spacer guides are commercially available, such as those sold by the firm ZIMMER USA, of Warsaw, Ind.

If such tibial alignment and spacer guides up to now have proved to be of substantial help in the implantation of total knee prosthesis with a given configuration and a non adjustable thickness, unfortunately they are not of the same help and interest for use in the implantation of a total knee prosthesis such as disclosed in the above mentioned copending application Ser. No. 4,556, which prosthesis includes removable and replaceable condylar bearing members allowing the surgeon who installs the knee prosthesis to obviate misalignment naturally existing in the patient's knee or resulting from faulty sectioning of the patient's bones during fixation of the prosthesis.

As a matter of fact, in such "adjustable" knee prosthesis, the use of a tibial alignment guide and of a spacer guide of a given thickness is not of a particular interest since any misalignment or variation in thickness in the lateral direction may be corrected by the implantation of bearing members of different thicknesses. However, implantation of bearing members of different thicknesses involves tests for determining the appropriate thickness of each bearing member and checking whether or not the prosthesis with the selected bearing members fits the resected zone properly.

It is an object of the present invention to provide a multi purpose tibial template useful in the implantation of an adjustable total knee prosthesis including interchangeable condylar bearing members, for determining the appropriate thickness of the bearing members and testing the same.

It is another object of the invention to provide a multi purpose tibial template which may further be used in total knee arthroplasty as either conventional tibial alignment or spacer guide, for determining the desired location of the tibial prosthesis component on the patient's tibia, the width or the amount of tibial eminence to be preserved, the planes of tibial plateau osteotomies, the location of the fixation studs of the tibial prosthesis component and the appropriate thickness of the tibial prosthesis component to be used.

These objects are achieved with a multi purpose tibial template comprising:

a Y-shaped element comprising a flat handle integrally extended at one end by two flat, elongated prongs, which elongated prongs are symmetrically arranged with respect to a vertical plane passing through the axis of the Y-shaped element perpendicularly to the general plane thereof;

an alignment rod fixable onto the flat handle near its integrally extended end, which alignment rod is substantially perpendicular to the general plane of the Y-shaped element; and a set of provisional plateaus of different thicknesses for each prong, for determining the thickness of the condylar bearing members to be used in the total knee prosthesis.

Each prong has substantially the same contour as each of the elongated sections of the tibial component on which lie the condylar bearing members of the prosthesis to be implanted, respectively, and comprises a central hole extending perpendicularly to the general plane of the Y-shaped element.

Each provisional plateau comprises an upper concave surface having substantially the same shape and contour as the upper surface of the condylar bearing member of the knee prosthesis to which it corresponds, and a lower flat surface downwardly extended by a central projection insertable in the central hole of the prong corresponding to this plateau, to retain the latter onto the prong, when necessary.

Preferably, the elongated prongs together define a U-shaped recess allowing for retention of the natural intercondylar eminence of the patient's tibia, in use. As preferably, they are both of a slightly smaller thickness than that of the handle, and define two rounded shoulders useful for positioning the tibial template onto the patient's tibia and locating and retaining the provisional plateaus and tibial component of the total knee prosthesis onto the surface of the Y-shaped element, when testing the same.

When the multi purpose tibial template according to the invention is used in the implantation of an adjustable total knee prosthesis further including two central studs extending downwardly from the lower surfaces of the elongated sections of the tibial component, respectively, to allow for better anchoring of the same in the patient's tibia, then the central holes in the elongated prongs are preferably positioned in cooperative relationship with respect to the studs of the tibial component of the prosthesis and have substantially the same contour as these studs to help in locating the same.

The invention will be better understood with reference to the accompanying drawings, wherein.

Figure 1:
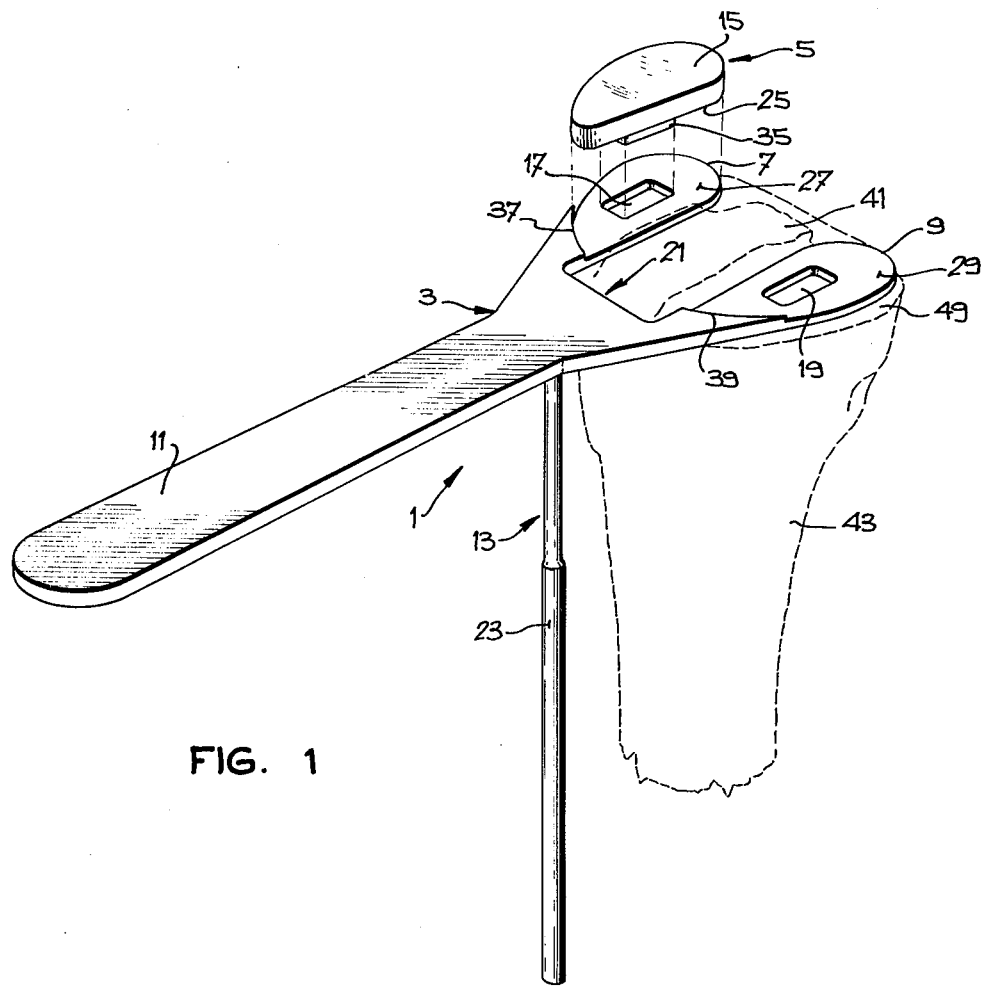
FIG. 1 is a perspective view of an embodiment of the multipurpose tibial template according to the invention, shown in use.

Referring to FIG. 1, the multipurpose tibial template 1 for use in the implantation of a total knee prosthesis, essentially comprises a Y-shaped element 3 with a flat handle 11 and two symmetrically arranged prongs 7 and 9 integrally extending at one end of the flat handle 11, an alignment rod 13 fixable onto the flat handle 11 perpendicularly thereto near its integrally extended end, and a set of provisional plateaus 5 of different thicknesses for each prong 7 or 9.

The tibial template is especially designed for use in the implantation of an adjustable knee prosthesis such as disclosed and claimed in copending patent application Ser. No. 4,556 in the name of the same inventor, which prosthesis includes a femoral component 55 to be anchored in the femur 53 of a patient (see FIG. 4) to replace the natural, medial and lateral femoral condylars, and a tibial component 45 to be anchored in cooperative relationship with respect to the femoral component 55 in the patient's tibia 43 (see FIG. 5), to replace the natural medial and lateral tibial plateaus 47 and 49, respectively.

Figure 5:
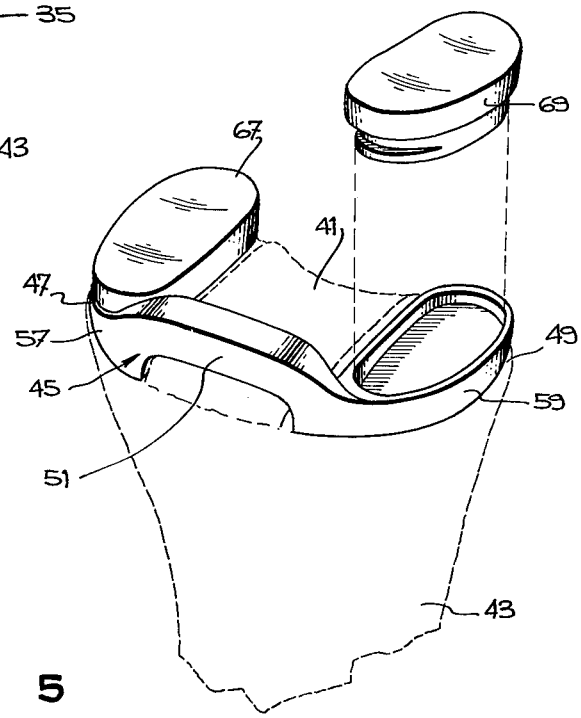
FIG. 5 is a perspective view of the tibial component of a total knee prosthesis once it has been positioned onto the tibial of a patient, using the tibial template shown in FIG. 1.

As is shown in FIG. 5, the tibial component 45 comprises a platform member consisting of two spaced apart, tray-shaped sections 57 and 59 connected by a bridge section 51, and two removable and replaceable condylar bearing members 67 and 69 lying on and retained by the tray-shaped sections 57 and 59, respectively. In use, the tray-shaped sections 57 and 59 which are symmetrical and both of a substantially ovoidal configuration are fixed onto the patient's tibia 43 after having removed the upper surfaces of the natural plateaus 47 and 49 by conventional tibial osteotomy.

Preferably, the natural intercondylar eminence 41 of the patient's tibia, which normally extends between the natural tibial plateaus 47 and 49 and helps in stabilizing the knee, is preserved during the osteotomy and left in the space defined between the spaced-apart, tray-shaped sections 57 and 59.

The removable condylar bearing members 67 and 69 which are both of an ovoidal shape matching with that of the respective tray-shaped sections 57 and 59 but may be of different thicknesses, are advantageously replaceable, thus allowing the surgeon who installs the prosthesis to obviate misalignment naturally existing in the patient's knee or resulting from faulty sectioning of the patient's bones during fixation of the prosthesis.

As emphasized in the preamble of the present specification, the tibial template 1 is used in particular for determining the appropriate location of the tibial component 45 on the patient's tibia 43, the width or the amount of tibial eminence 41 to be preserved before fixing the tibial component 45 and the planes of the tibial plateaus 47 and 49 during the tibial osteotomy.

For these purposes, the prongs 7 and 9 of the Y-shaped element 3 which are both flat and extend in the same plane as the handle 11, are shaped so as to have substantially the same ovoidal contours as the elongated sections 57 and 59 of the tibial component 45. The so shaped prongs 7 and 9 together define a U-shaped recess 21 which is substantially of the same width as the space defined by the elongated sections 57 and 59 of the tibial component 45. The recess 21 receives the natural intercondylar eminence 41 of the patient's tibia 43.

Figure 2:
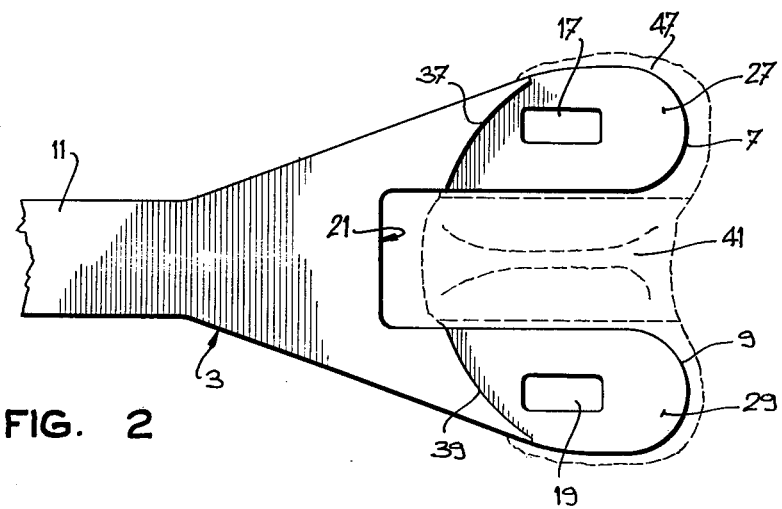
FIG. 2 is a top plan view of a part of the Y-shaped element of the tibial template of FIG. 1, in use.

During the operation, the prongs 7 and 9 are first used to determine the appropriate position that should have the tibial component. To help the surgeon in this determination, the upper surfaces of the prongs 7 and 9 comprise two symmetrical shoulders 37 and 39 (see FIG. 2) which together figure the frontal periphery of the tibial component 45 to be implanted. The U-shaped recess 21 defined by the prongs 7 and 9 then is used to determine the width of intercondylar eminence 41 that may be preserved, before installing the tibial component 45. After removal of the upper surfaces of both tibial plateaus 47 and 49, the flat prongs 7 and 9 then are used again on the resected portions of the patient's tibia 43 to check the planes of the same. The alignment rod 13 which is fixed onto the flat handle 11, helps in so checking the planes of the resected plateaus. Actually, the alignment rod 13 must be parallel to the long axis of the tibia 45 when viewed laterally (see FIG. 3) and coincide with the long axis of the tibia when viewed anteriorly, to ensure correct positioning of the tibial component 45 onto the patient's tibia 43. Of course, ajustments can be made, if necessary.

As also emphasized in the preamble of the present specification, the tibial template 1 may also be used as provisional tibial prosthesis component for trial reduction and test for range of motion.

For this purpose, use is made of the sets of provisional plateaus 5. Each set includes several plateaus 5 all having upper surfaces both substantially the same shape and contour as the upper surface of condylar bearing members 67 and 69, but different thicknesses. Each set is intended to be used in association with one prong and therefore each of its plateaus 5 comprises an upper surface having the same specific shape and contour as the condylar bearing member matching with the tray-shaped section of the tibial component 45, to which the one prong corresponds.

For example, the provisional plateau 5 illustrated in FIG. 1 comprises an upper surface 15 having substantially the same shape and contour as the condylar bearing member 67 which matches with the tray-shaped section 57 to which the prong 7 corresponds. This plateau 5 also comprises a lower flat surface 25 having substantially the same contour as the upper surface 27 of the prong 7. This lower flat surface 25 is downwardly extended by a central projection 35 having a rectangular shape and a height smaller than the thickness of the prong 7.

The central projection 35 is intended to facilitate positioning and retainment of the provisional plateau 5 onto the prong 7. For this particular purpose, the prong 7 has a central hole 17 extending perpendicularly to the general plane of the Y-shaped element 3, which hole is especially designed for receiving the projection 35. As can be easily understood, the hole 17 and projection 35 are located in such a position with respect to the upper surface of the prong 7 and the lower surface of the plateau 5 respectively, that, on one hand, the lower flat surface 25 of the plateau 5 does not extend beyond the upper surface 27 of the prong 7 and, on the other hand, the upper concave surface 15 of the plateau 5 is exactly in the position in which will be the corresponding intercondylar bearing member 67, once the operation is completed.

Of course, the other prong 9 of the tibial template 1 similarly comprises a central hole 19 passing through its upper surface 29, for receiving the central projection 35 of each of the plateaus of its own set.

Figure 4:
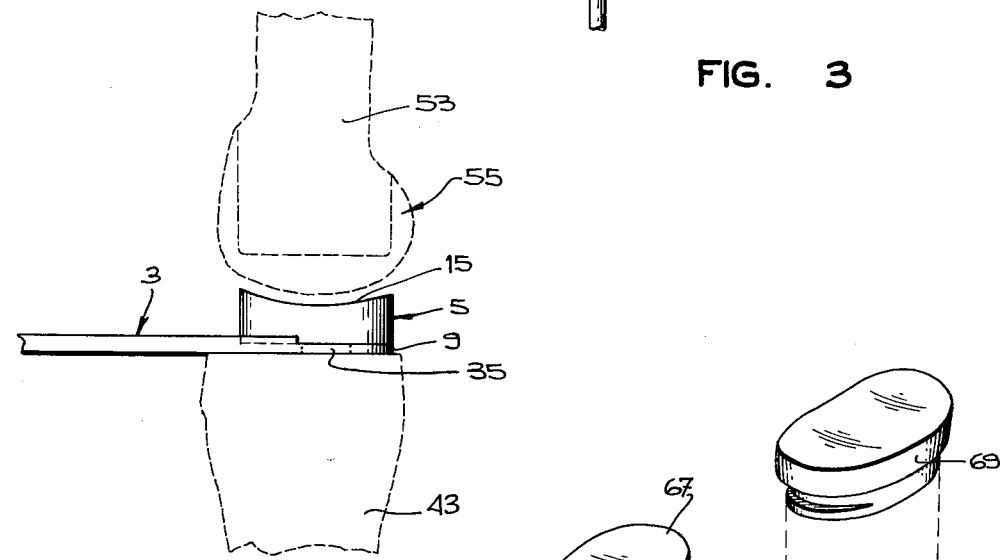
FIG. 4 is an elevational side view of the tibial template of FIG. 1, in use for determining the appropriate thickness of the bearing members of a total knee prosthesis.

During the operation, the provisional plateaus 5 are advantageously used after the implantation of the femoral component 55 (see FIG. 4). A plateau 5 of appropriate thickness is first selected in each set. The two selected plateaus 5 are then positioned onto the prongs 7 and 9, by means of their projections 35, and the tibial template 1 is inserted into the joint and leaned onto the resected tibial plateaus (see FIG. 4). In this position, the tibial template 1 may advantageously be used as provisional tibial component, owing to its prongs which are substantially of the same shape and contour as the tray-shaped sections of the tibial component 45 and to its provisional plateaus which have upper concave surfaces of the same shape and contour and in the same position as the upper surfaces of the condylar bearing members 67 and 69. This allows for various tests for checking the range of motion of the prosthesis joint.

This also, and more essentially, allows for easy fast and accurate determination of the appropriate thickness that must have each of the condylar bearing members 67 and 69 to avoid prejudiciable misalignment between the tibial and femoral prosthesis components. Actually from the respective thicknesses of the provisional plateaus 5 that may be tested with the tibial template 1, the surgeon may easily determine the appropriate thicknesses that must have the condylar bearing members 67 and 69. To help the surgeon in his determination the provisional plateaus 5 may for example, be numbered, each number corresponding to a thickness for the condylar bearing members.

At last, the multi purpose tibial template 1 may be used for testing the tibial component 45 and for determining the location of the fixation studs extending downwardly from the lower surfaces of the tray-shaped sections 57 and 59 of the same, if any.

For these purposes, it is necessary that the shoulders 37 and 39 defined on the upper surfaces of the prongs 7 and 9 for figuring the frontal periphery of the tibial component 45, and the central holes 17 and 19 passing through the prong 7 and 9 respectively, for receiving the projections 35 of the provisional plateaus 5, be respectively so located and dimensioned as to allow for reception, engagement and holding of the tibial component 45 and its studs onto the prongs.

Accordingly, the central holes 17 and 19 are located with respect to the upper surfaces 27 and 29 of the prongs 7 and 9 respectively, so as to be at the same position as the studs with respect to the lower surfaces of the tray-shaped sections of the tibial component 45. The central holes 17 and 19 are also dimensioned so as to receive the studs. This allows for not only fast and easy positioning and holding of the tibial component 45 onto the tibial template 1 by insertion of the studs into the central holes of the prongs, but also, using the central holes which are located at the same places as the studs, easy location and determination of the surfaces 79 of the resected tibial plateaus that must be bored to receive the studs.

Figure 3:
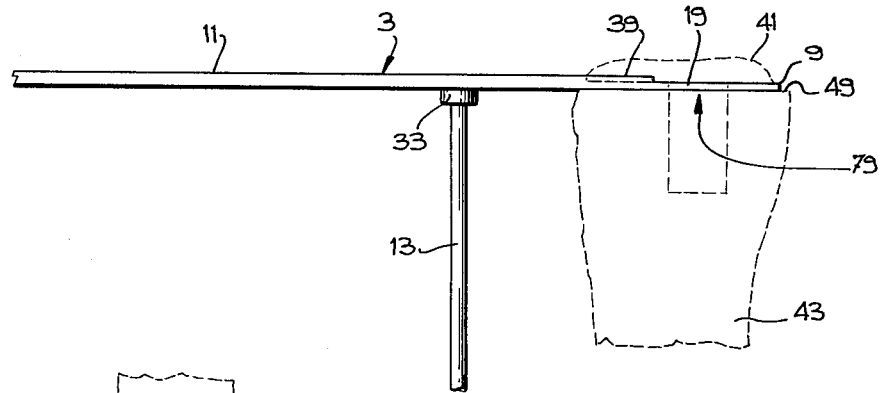
FIG. 3 is an elevational side view of the Y-shaped element partially shown in FIG. 2.

The shoulders 37 and 39 which both result from a difference of thickness between the ends of prongs 7 and 9 and the handle 11 respectively, as is clearly shown in FIGS. 1, 3 and 4 of the drawings, are shaped and located with respect to the general surface of the Y-shaped element 3, and more especially the prongs 7 and 9, so as to receive and match with the front end of the tibial component 45. This also helps in positioning and holding the tibial component 45 onto the tibial template 1, which then can be easily inserted and tested into the joint before definitive implantation.

As some of the various determination and tests that may be carried out with the tibial template 1, such as the determination of the appropriate thicknesses of the condylar bearing members or the location of the surfaces of the resected tibial plateaus to be bored to fix the studs, do not require the use of the alignment rod 1, the latter is fixed in a removable manner onto the Y-shaped element 3. For this purpose the upper end of the alignment rod 13 is threaded and may be screwed into a small nut 33 (see FIG. 3) welded on the bottom surface of the Y-shaped element. Preferably, a portion 23 of the alignment rod 13 has its surface corrugated to allow for better grasping of the same.

In the course of a total knee arthroplasty, the above described tibial template 1 may be used as follows.

First of all, the tibial template is placed on the patient's tibia 43 to determine the sites of vertical osteotomies along the tibial eminence, which sites may be easily marked with methylene blue and serves as guide references.

Once the upper surfaces of the natural tibial plateaus are removed using an appropriate osteotome or a conventional oscillating saw, the tibial template 1 is placed on the resected plateaus to check the resection, using the alignment rod 13 as a guide.

Once the femoral component 55 is fixed onto the patient's femur 53 the tibial template 1 is provided with a set of appropriate provisional plateaus 5 and is placed again on the resected tibia with its alignment rod in line with the patient's tibia. This operation is carried out with the knee in acute flexion. Thereafter, the leg is slowly extended and adjustments in the cut can be made if extension becomes too difficult. The stability, axial alignment and movements of the prosthesis can thus be checked and the necessary corrections be made. According to the thicknesses of the provisional plateaus 5 which have proved to be the most appropriate, easy and accurate determination of the thicknesses of the condylar bearing members 67 and 69 to be implanted in the tibial component 45 is made.

When the above operation is completed, the provisional plateaus 5 are removed from the tibial template 1 and the instrument is reinserted in the joint. The central holes 17 and 19 are then used to determine the locations of the fixation studs of the tibial component on the resected plateaus prior to piercing the stud receiving holes in the tibia 43 with a drill. These locations can be marked with methylene blue.

At last, the tibial template 1 is used to test the tibial component 45 prior to fixing it onto the patient's tibia 43 and to check its mediolateral position in relationship to the femoral component.

Therefore, one can see that the tibial template 1 actually is a multi purpose template which is of a great interest in the implantation of a total knee prosthesis because of its simple structure and its variety of functions.

I claim:

1. A multipurpose tibial template for use in the implantation of an adjustable total knee prosthesis including a femoral component and a tibial component comprising a platform member consisting of two spaced apart, elongated sections connected by a bridge section, and two removable and replaceable condylar bearing members lying on and retained by the two elongated sections respectively, said tibial template comprising:

a Y-shaped element comprising a flat handle integrally extended at one end by two flat, elongated prongs, said elongated prongs being symmetrically arranged with respect to a vertical plane passing through the axis of the Y-shaped element perpendicularly to the plane thereof, each prong having substantially the same contour as each of the elongated section of the tibial component to be implanted, respectively, and comprising a central hole extending perpendicularly to the plane of the Y-shaped element;

an alignment rod fixable onto said flat handle near its integrally extended end, said alignment rod being substantially perpendicular to the plane of the Y-shaped element; and a set of provisional plateaus of different thicknesses for each prong, for determining the thickness of the condylar bearing members to be used in the total knee prosthesis, each provisional plateau comprising an upper concave surface having substantially the same shape and contour as the upper surface of the condylar bearing member of the knee prosthesis to which it corresponds, and a lower flat surface downwardly extended by a central projection insertable in the central hole of the prong corresponding to said plateau to retain the latter onto said prong.

2. A multipurpose tibial template as claimed in claim 1, wherein the elongated prongs together define a U-shaped recess allowing for retention of the natural intercondylar eminence of the patient's tibia in use.

3. A multipurpose tibial template as claimed in claim 2, wherein the elongated prongs are both of a slightly smaller thickness than that of the handle, and define two rounded shoulders useful for positioning the tibial template onto the patient's tibia and for locating and retaining the provisional plateaus and tibial component of the total knee prosthesis onto the surface of the Y-shaped element, when testing the same.

4. A multipurpose tibial template as claimed in claim 1, for use in the implantation of an adjustable total knee prosthesis further including two central studs extending downwardly from the lower surfaces of the elongated sections of the tibial component, respectively, to allow for better anchoring of the same in the patient's tibia, wherein the central holes in the elongated prongs are positioned in cooperative relationship with respect to the studs of the tibial component of the prosthesis and have substantially the same contour as said studs to help in locating the same.

* * * * *